(12) United States Patent
Janzen et al.

(10) Patent No.: US 8,252,605 B2
(45) Date of Patent: Aug. 28, 2012

(54) METHOD AND COMPOSITION FOR STABILIZING LIQUID REAGENTS

(75) Inventors: Roland Janzen, Landenberg, PA (US); Carsten Ulrich Schelp, Hockessin, DE (US)

(73) Assignee: Siemens Healthcare Diagnostics Inc, Tarrytown, NY (US)

( * ) Notice: Subject to any disclaimer, the term of this patent is extended or adjusted under 35 U.S.C. 154(b) by 567 days.

(21) Appl. No.: 12/431,575

(22) Filed: Apr. 28, 2009

(65) Prior Publication Data

US 2009/0208987 A1    Aug. 20, 2009

Related U.S. Application Data

(62) Division of application No. 10/720,909, filed on Nov. 24, 2003, now abandoned.

(51) Int. Cl.
  *G01N 33/543*    (2006.01)
(52) U.S. Cl. ...................................................... 436/518
(58) Field of Classification Search .................. None
  See application file for complete search history.

(56) References Cited

U.S. PATENT DOCUMENTS

| | | | |
|---|---|---|---|
| 3,645,852 A | 2/1972 | Axen et al. | |
| 4,081,402 A * | 3/1978 | Levy et al. | 428/36.4 |
| 4,686,181 A | 8/1987 | Dona | |
| 4,914,040 A | 4/1990 | Lenz et al. | |
| 5,039,607 A | 8/1991 | Skold et al. | |
| 5,278,081 A | 1/1994 | Deger et al. | |
| 5,395,938 A | 3/1995 | Ramakrishnan | |
| 5,567,591 A | 10/1996 | Lovell et al. | |
| 5,658,725 A | 8/1997 | Schlieper et al. | |
| 5,705,338 A | 1/1998 | Piran et al. | |
| 5,863,740 A | 1/1999 | Kientsch-Engel et al. | |
| 5,919,642 A | 7/1999 | Khanna et al. | |
| 5,952,185 A | 9/1999 | Huber et al. | |
| 5,965,378 A | 10/1999 | Schleiper et al. | |
| 6,087,188 A | 7/2000 | Johansen et al. | |
| 6,303,325 B1 | 10/2001 | Harshvardhan et al. | |
| 6,406,913 B1 | 6/2002 | Ullman et al. | |
| 7,615,340 B2 * | 11/2009 | Bamdad | 435/6.11 |
| 2002/0028519 A1 * | 3/2002 | Yguerabide et al. | 436/518 |

FOREIGN PATENT DOCUMENTS

WO    9522766    8/1995

OTHER PUBLICATIONS

Elkon, KB, Capillary Blotting and Contact Diffusion, CRC Handbook of Immunoblotting of Proteins, vol. 1, Chapter 4.1, pp. 51-59, O.J. Bjerrum & N.H.H. Heegaard, Eds., CRC Press, Inc. 1988.
Dittmer, J. et al, A Native, Affinity-based Protein Blot for the Analysis of Streptavidin Heterogeneity: Consequences for the Specificity of Streptavidin Mediated Binding Assays. Electrophoresis, 1989; 10:762-765.
Bittner, M. & Rowold, E., Electrotransfer in Equipment Containing Buffer, in CRC Handbook of Immunoblotting of Proteins, vol. 1, Chapter 4.3.1, pp. 69-77, O.J. Bjerrum & N.H.H Heegaard, Eds., CRC Press, Inc. 1988.
Lodish et al., Molecular Cell Biology, Section 2.3, W.H. Freeman & Co. (2000) (retrieved Jan. 26, 2007, from http://www.ncbi.nlm,gov). 12 printed pages.

* cited by examiner

*Primary Examiner* — Ann Lam
(74) *Attorney, Agent, or Firm* — Theodore J. Leitereg

(57) ABSTRACT

The invention relates to methods and compositions for removing a dissociated species from a fluid medium solution during and after it has detached from a solid-phase immersed in said medium, thereby allowing the concentration of free species to remain close to zero, and for improving the signal to noise ratio in assays. This is achieved by employing a substrate, such as a scavenging solid-phase, having an attached binding partner or partners ("scavenger") for the specifically binding species and which is present during storage. This substrate may also contain regions for binding signal generating components attached to the solid-phase. This substrate binds any free species bleeding off the solid phase, increasing the reliability and sensitivity of assays. A subset of the substrates in the invention additionally forms cross-linked networks of solid-phase particles that further increase the sensitivity of assays.

6 Claims, No Drawings

METHOD AND COMPOSITION FOR STABILIZING LIQUID REAGENTS

This application is a divisional of U.S. Ser. No. 10/720,909, filed Nov. 24, 2003 now abandoned.

FIELD OF THE INVENTION

The present invention relates to methods and compositions for improving the signal to noise ratio in assays and stabilizing liquid reagents through the entrapment of free binding species in a reagent solution or suspension. In particular, the present invention provides a method for increasing signal strength by forming signal generating networks as well as a method for immobilizing free binding species in a reagent solution through the use of a binding substrate having selectivity for binding the species of interest.

BACKGROUND OF THE INVENTION

In modern in-vitro clinical diagnostics, a variety of methods are utilized for the detection of analytes in a sample. In one form of a diagnostic method, an immunoassay, one or more specifically binding species are used. Typical examples are the sandwich immunoassay, where two specifically binding species (antibody or antigen) bind to the analyte of interest, and the competitive immunoassay, where the analyte of interest and an analog of this analyte compete for binding to a specifically binding species. One of the specifically binding species is commonly attached to a so-called label or tag, which may be an atom (e.g., radioactive), molecule (e.g., an enzyme, fluorescent, or luminescent compound) or particle (magnetic or latex). This label allows for detection of the analyte of interest through a variety of detection methods corresponding to the label utilized. In a competitive assay, either the specifically binding species or the analyte analog can carry the label.

The other specifically binding species is frequently associated to a solid or suspendable substrate ("the solid phase") covalently or through adsorption. Alternatively, it may be linked to a first member of a second binding pair (e.g., biotin), while the second member of the second binding pair (e.g., streptavidin) is attached to the solid phase. This allows the specifically binding species to bind to the solid phase via the second binding pair interaction (e.g., biotin-streptavidin).

Solid phases may be macroscopic solid phases, such as microtiter well, tube and ball in tube devices, or suspendable solid phases, such as beads, latex beads, magnetic latex beads, as well as other paramagnetic materials. A secondary binding species is commonly labeled through the use of a tag. The interaction between the tag and the solid phase allows for detection and quantification of the analyte of interest through a variety of detection methods corresponding to the label utilized.

It is important for the stability and reproducibility of the diagnostic assay that the binding ability of the solid-phase bound species for its binding partner does not become impaired over time. This may result in decreased reliability and decreased assay sensitivity. One mechanism that may lead to such impairment (apparent as instability) is bleeding of a portion of the solid-phase-attached species into the surrounding medium. The free species competes with the solid-phase-attached species for binding to the target and usually has a significant kinetic advantage due to its faster diffusion. Therefore, it is advantageous to maintain the amount of free species competing with the solid phase-attached species in a reagent constant, preferably very close to zero. This would allow for the sensitive detection of analytes in a stable and reproducible manner. The preferred way of eliminating free species is to find a binding method that will eliminate dissociation. Covalent bonding, as opposed to adsorptive association, might be the method of choice, due to its greater bond strength. However, in many cases this may be impossible or impractical, for various reasons.

For example, the material chosen for the solid-phase may lack suitable active groups for covalent coupling. If that is the case, due to the type of assay, or for cost considerations, adsorption will then be the preferred choice of association. An alternative method involves having a binding species that is attached to the solid-phase material indirectly through an auxiliary binding species. An example of this would be a biotinylated antigen or antibody that is attached to an avidin coated substrate, avidin being the auxiliary species. The auxiliary binding species itself can be associated with the solid phase via a covalent bond or by adsorption. This method may be utilized when the binding species becomes inactivated if directly associated with the solid-phase material. Again, since the affinity constant of the auxiliary binding species is not infinite, some dissociation, in the form of bleeding, may occur.

A further method includes binding species consisting of subunits which are either non-covalently associated with each other or have a covalent bond that is reversible under normal storage conditions. Subunits that are in this way reversibly and indirectly attached to the solid phase can disassociate from the surface-coupled subunit(s). If the free subunit retains its binding ability in the assay, or regains it after combining with other free subunits, the free subunit may interfere in the assay.

If bleeding cannot be eliminated, several practices, each with its particular disadvantages, have been employed to compensate for bleeding, including the following:

1) Frequent recalibration to correct for the drift caused by bleeding of the binding species. The most obvious disadvantage is additional cost for reagent and time spent on recalibration. The bleeding may also limit shelf life due to assay signals dropping to insufficient levels.

2) Supplying the immunoassays and other diagnostic assay reagents in a dried form, such as lyophilized or air-dried product. This approach usually eliminates bleeding, but dry reagents typically need to be reconstituted by addition of liquid, which requires time and effort by a user. The drying process itself requires additional processing by the manufacturer and introduces a source of inhomogeneity and bottle-to-bottle variation not found in reagents in a liquid form. The drying process may also increase lot-to-lot variation.

3) If the solid phase is stationary (e.g. microtiter plate) or can be conveniently separated from the liquid (magnetic beads or other, larger or smaller sized beads), it is possible to "wash" the reagent with water or an appropriate liquid before beginning the assay. A disadvantage of this approach involves the additional time, effort, and materials required for a "pre-wash" step and the limits imposed on flexibility in designing the assay sequence.

U.S. Pat. No. 5,212,063 discloses a ligand trap useful for reducing or eliminating biotin interference in immunoassays that employ biotin labeled antibodies (or other biotinylated species). Biotin, which naturally occurs in body fluids, can compete with the biotinylated species for binding sites on the avidin or streptavidin conjugate employed in these assays and cause erroneous results. Biotin is selectively removed from the immunological reaction by incubating the sample solution with polymer particles consisting of a streptavidin-modified core and a biopolymer coating.

U.S. Pat. No. 5,863,740 discloses an interference-eliminating agent through the modification and inactivation of Streptavidin molecules by biotin saturation, chemical modification or genetic engineering.

U.S. Pat. No. 4,256,834 discloses a fluorescent scavenger particle immunoassay. A reagent employed in the reaction contains a signal repressor. This signal repressor interacts with a label connected to a member of a signal producing system in bulk solution. Upon coupling of the label and member of the signal producing system to the homologous member of the signal generating system, the signal repressor no longer interferes.

If the attachment of the binding species to its solid phase is not irreversible, and the potential remedies discussed above are not an option, a certain amount of the binding species will be released into the fluid medium. This may lead to impairment of the assay, typically evidenced as instability.

The situation is further exacerbated because production of reagents typically occurs a significant amount of time prior to their actual use. This creates the necessity of storing the assay reagents under a variety of conditions. During storage and transport, there may be irregularities in temperature, which may detrimentally affect the release of solid-phase bound species. These variables of time, temperature and motion all contribute to the dissociation of the binding species from the solid-phase material.

Although dissociation will primarily take place prior to utilization of the assay reagents, the impairment will result when a sample, such as a bodily fluid, is added. The dissociated species will then compete with the solid-phase attached species for binding to the target and usually has a significant kinetic advantage due to its faster diffusion rate. When the amount of target is limited, even a small amount of free material can significantly reduce the number of targets bound to the solid phase. This, in turn, can yield false results that, even when detected, will require reruns and recalibration.

It is therefore highly desirable to keep the amount of free species in reagents constant, preferably very close to zero. When permanent association of the binding species to the solid-phase is physically impossible or economically prohibitive, a remedy must be provided to avoid instability that can result in incorrect test results.

SUMMARY OF THE INVENTION

The present invention offers a solution by providing methods and compositions for improving the reliability and sensitivity of assays. In one embodiment, this solution is achieved by stabilizing assay reagents by immobilizing a dissociated species from a fluid medium solution during and after the species has detached from a solid-phase, thereby allowing the concentration of free species to remain close to zero. This is accomplished by using a substrate, such as a scavenging solid-phase, having an attached binding partner or partners ("scavenger") for the specifically binding species which is present in the reagent during storage. This substrate binds any free species bleeding from the solid phase and prevents such species from interfering with the assay.

In another embodiment, a solution is achieved by amplifying the immunoassay reaction signals generated in an assay. Amplification is produced by using a substrate including multiple binding sites for binding pair members attached to a solid-phase. Binding pair members bound to a solid-phase may attach to common particles of substrate thereby cross-linking signal generating components associated with the binding pair members of the solid phase. This aggregation of solid phase binding pair members forms a signal-generating network, greatly amplifying signal strength. In order to maximize reliability and sensitivity of assays, it is preferable to provide a single substrate that immobilizes a dissociated species and also aggregates solid phase binding pair members to produce a signal-generating network. This network can also be created by introducing proteins or polymers with multiple binding sites for the binding pair members, whereas the proteins or polymers are conjugated with multiple binding sites for the binding pair members. Bovine serum albumin (BSA), human serum albumin (HSA), antibodies, or polymerized BSA, polymerized antibodies, dextrans, and dendrimers can function as such carriers for multiple binding sites.

The present invention therefore encompasses a reagent including a fluid medium containing a first substrate having an attached first binding species. Further, a second substrate is included having regions for selectively binding the first binding species if dissociated from the first substrate, and may also include multiple binding sites for binding pair members attached to the first substrate.

DETAILED DESCRIPTION OF THE INVENTION

It is essential that the scavenging substrate of the present invention fulfill a number of criteria, including but not limited to:

1) If the material chosen is porous, the pores must be large enough to allow the free species to diffuse into the pore system, where the scavenger substrate captures it.

2) If the solid-phase is a suspendable material, the scavenger substrate must allow for retention of the free species, while not attaching to the suspendable solid-phase material in a way that detrimentally affects signal strength or binding of the binding target to the solid-phase bound species.

3) The number and affinity of scavengers in the scavenger substrate must be sufficient to capture and retain free binding species that may bleed off the solid-phase during shelf life of the product.

4) The scavenger substrate must not interfere with a pipetting procedure. Therefore, it is either connected to the reagent storage vessel, separated out before pipetting (including settling out by sedimentation) or of a size that is small enough to pass through the pipetting device.

5) If the scavenger substrate is pipetted with the reagent to be stabilizes, the scavenger substrate must not interfere with the reactions that are part of the assay; i.e., apart from attached scavengers, the scavenger substrate should be largely inert to all relevant constituents of the assay.

6) Further, if the scavenger substrate is pipetted with the reagent it stabilizes, the scavenger substrate must not interfere with the detection system. In cases where the scavenger substrate is capable of interfering with the detection, the substrate must be removable before the detection by common methods such as sedimentation, filtration, or magnetic separation.

7) The scavenger substrate must be sufficiently stable so that any amount of scavenger bleeding from the scavenger substrate will be too small to interfere with the assay.

In one embodiment of the present invention, a method and composition is provided which can improve the stability of liquid reagents used in immunoassays or other in-vitro diagnostic methods. It provides means to remove or neutralize binding species that dissociate by bleeding or leaching from a surface or other solid-phase used in the device, which otherwise may interfere with the assay. In an exemplary instance, the present invention was applied to Streptavidin (SA) modified latex reagents, as used in a luminescent oxygen channeling immunoassay (LOCI™). Dyed and hydrophilically coated latex beads, covalently modified by coupling (SA) to their surface, are a useful generic reagent in LOCI™ immunoassays.

It has been unexpectedly discovered that many reagent compositions slowly release SA upon storage in suspension even though it was not possible to detect physically adsorbed material or the breakage of covalent bonds linking the SA to the beads as well as to other materials, such as SA on chrome particles with a hydrophilic coating or on latex with a magnetic core. Possibly the subunit structure of SA allows for the dissociation of non-covalently bound SA subunits from the surface and re-association to intact SA in the solution. Since it appears that bleeding from the surface is due to an inherent property of SA, stabilization of the beads would be expected to be difficult.

In one example, a small amount of a porous substrate, covalently modified with biotin, was added. A polymeric material was chosen, such as those used for affinity chromatography (Toyopearl AF-Amino-650M, Lot 65NHM52W), with amino functional groups (90 µmol/mL), a pore size of ca. 100 nm (1000 Å), and a particle size of ca. 65 µm and biotin (sulfo-NHS-LC-biotin) was covalently coupled to the surface. The molar ratio of amino groups to biotin derivate was ca. 2 and the coupling medium was 0.15 M sodium bicarbonate. The material was sufficiently large to have a very small outer surface (<0.1 m$^2$/ml), which minimizes potential adsorption of SA beads. The pores are large enough (ca. 100 nm) to allow access for the SA molecule (ca. 5 nm), even after the pore structure becomes more narrow due to biotin modification, blocking protein and partial saturation with SA. At the same time, the pores are sufficiently small for the material to have a large internal surface area (>50 m$^2$/g) and corresponding high binding capacity, thereby minimizing the amount of scavenger beads required. The pores are also sufficiently small to exclude SA beads which are typically 200 nm or larger.

The parameters chosen for the scavenger substrate represent a potential optimum in terms of economy (if one wants to use as little scavenger as possible to stabilize the immunoassay reagent). However, a scavenger substrate with different particle sizes (from <100 nm to about 5 mm), different average pore size (e.g., between 50 and 5000 Å), different functional group type and density, would also work under appropriate circumstances.

In one example, biotin coupled scavenger substrate, such as Toyopearl beads, were added to an SA bead reagent (with a concentration of 1400 ug beads/ml) at a concentration of approximately 0.350 µl of settled bead volume per ml of reagent. The beads were initially mixed by vortex and then stored in wells within Flex™ reagent container, available from Dade Behring Inc., Deerfield, Ill., without further agitation. The scavenger beads settled to the bottom of wells and acted from there. The SA bead reagent was prepared using a Toyopearl, Bead (AF-Amino-650M, Lot 65NHM52W) having 65 um bead size, 300 A pore size, 90 umol/mL of amino-group on the surface (a product of Tosoh Haas, available from Sigma) and biotin-LC-NHS (Sulfo) from Pierce.

The following procedure was followed:
1. Add 1 mL of Toyopearl bead suspension (ca. 0.7 ml settled beads) into a small end-capped column (yellow column with caps for wide and narrow end)
2. Wash the beads with 15-20 mL of NaHCO3 (0.15 M).
3. Add 1 mL of 0.15 M NaHCO3 solution and vortex to re-suspend the beads.
4. Dissolve 20 mg of Biotin-LC-NHS (sulfo) into 1 mL of DI-water.
5. Add (4) into (3) with vortex.
6. Rotate the end-capped column at room temperature over night (about 24 hr).
7. Add 50 mg of BSA to the solution and rotate the column at room temperature over night.
8. Wash the beads with 30 mL of 50 mM HEPES buffer, pH 7.5.
9. Add 2 mL of HEPES buffer to re-suspend the beads.

The results of the stability study (TABLES 1 and 2) show that the release of SA at 4° C. leads to a decrease in recovery in a TSH assay. When the SA beads are centrifuged ("washed") after the 35 days to remove the free SA, the original quantitation is obtained. The SA is therefore the cause of the apparent instability. In the presence of scavenger beads, there is a slight initial increase due to the scavenger beads binding a small amount of SA that is free at the beginning of the study, After that initial period, the recovery remains constant as the scavenger beads maintain the amount of free SA close to zero.

In another exemplary embodiment, the scavenger substrate comprised a non-porous material, for example a surface, modified in a way that SA has access, but modified beads do not. A material, having indentations, such as crevices and other unpatterned design may also be used. Alternatively, or in conjunction with the other textures, grooves may be used to function in a manner similar to the porous substrate. Further, the substrate may be of a brush-like configuration, whereby the dissociated free species may migrate past the brush-like appendages and bind to the interior of the substrate. The solid-phase material, due to size difference would not enter into the binding area of the brush-like substrate.

A further embodiment may consist of a non-porous substrate having the ability to bind the free, dissociated species due to its weight, diffusion rate and other characteristics of the dissociated molecule, not apparent in the solid-phase bound species.

In an even further embodiment, a substrate may have multiple binding sites for the binding pair members attached to the solid-phase. This substrate may preferably, although not necessarily, possess the free-species scavenging properties discussed above. The multiple binding sites allow binding pair members from a plurality of solid-phase particles to attach to common substrate particles. In this manner, the substrate allows for cross-linking of the binding members on the solid phase. The cross-linking creates a signal generating network that improves the sensitivity of assays and the signal to noise ratio by forming particle aggregates. These particle aggregates further lead to an amplification of the assay signal through the signal generating networks.

As previously discussed, SA bleeds from the SA-modified reagents during storage leading to decreased assay sensitivity and reliability. In order to solve this problem, biotin was coupled to dyed sensitizer beads. In one example, the biotinylated sensitizer beads were prepared by the following method: uncoated dyed sensitizer bead lot 1053:89 was activated with EDAC followed by NHS then reacted with biotin LC-PEO amine (+) trioxaundecanediamine (Pierce 21347 lot DH57849) at RT for 72 hours; final bead weight is 20 mg/mL; final buffer is 100 mM TRIS, 300 mM NaCl, 1 mM EDTA, 1 mg/mL BSA, 0.1% Triton x405, 0.01% Proclin 300 pH 8.0.

The biotin-modified beads were added to the SA reagent at different concentrations LOCI™ TSH and FT3 assays were chosen as model assays. The SA bead concentrations in the TSH and FT3 assays were 1400 µg/mL and 400 µg/mL, respectively. The biotin-modified sensitizer beads were added in concentrations of 1% and 5% (TSH: 14 µg/mL, 70 µg/mL; FT3: 4 µg/mL, 20 µg/mL) of the SA bead concentration. The mixtures were incubated overnight at 4° C. The TSH and FT3 calibrators were measured and compared using the different sensitizer bead suspensions in the respective immunoassay.

The results (TABLES 5 and 6) showed that, in the presence of the biotin-modified sensitizer beads, there was a substantial increase in the immunoassay response signal while background noise for TSH remained essentially unchanged. This indicates the formation of signal generating networks in addition to the successful scavenging of free species. The amplified signal strength was primarily the result of the signal generating networks. Good reproducibility of signals over the course of a stability study was primarily the result of the scavenging properties of the biotin-modified sensitizer beads.

A second substrate with scavenging and/or cross-linking properties, as described above, provides an almost universal solution for bleeding problems of compounds that represent one part of a specific binding pair. It provides a solution to assays where a fluid medium is utilized in conjunction with a first substrate having a first binding species that separates into a first portion and a second portion, the dissociated second portion being the free species. A second substrate is used, having regions adapted to selectively bind the second portion of the first binding species (free species) from the solution without interfering with the assay. Preferably, this second substrate cross-links the first substrate into aggregates to increase signal strength. The addition of the second substrate puts very few limitations on the nature of the "solid phase" and does not require any separation or washing steps or lyophilization. There is no need for short calibration periods to correct for the effect of free species and in many cases, the shelf life of the device may be significantly extended.

As previously described, TABLE 1 and TABLE 2 further describe the results of a 35 day TSH Assay Stability study. As can be seen from TABLE 1, the assay stability was measured in the absence of a scavenger substrate. The quantitation was performed on the same day using a curve generated with $-70°$ C. stored material. As can be seen between Calibration Levels 2 through 5, the analyte values reported by the assay degrade significantly over time.

TABLE 1

TSH Assay Stability (4° C. Storage)
in the absence of porous scavenger
Quantitation performed on the same day using
curve generated with −70° C. stored material.

| Calibrator | Day 0 | Day 7 | Day 14 | Day 21 | Day 35 | Day 35 (Washed) |
|---|---|---|---|---|---|---|
| Level 1 | −0.01 | −0.01 | −0.01 | −0.01 | 0.00 | 0.01 |
| Level 2 | 0.87 | 0.80 | 0.71 | 0.69 | 0.65 | 0.89 |
| Level 3 | 3.98 | 3.63 | 3.31 | 3.15 | 2.91 | 4.01 |
| Level 4 | 19.39 | 18.01 | 16.84 | 15.31 | 14.52 | 19.66 |
| Level 5 | 54.68 | 50.01 | 47.03 | 44.59 | 37.25 | 55.39 |

TABLE 2

TSH Assay Stability (4° C. Storage)
in the presence of porous scavenger
Quantitation performed for each day
using same calibration curve as TABLE 1

| Calibrator | Day 0 | Day 7 | Day 14 | Day 21 | Day 35 |
|---|---|---|---|---|---|
| Level 1 | 0.00 | −0.02 | −0.02 | −0.02 | −0.02 |
| Level 2 | 0.98 | 0.99 | 0.98 | 0.99 | 1.01 |
| Level 3 | 4.34 | 4.51 | 4.53 | 4.40 | 4.62 |
| Level 4 | 20.77 | 22.11 | 22.08 | 21.62 | 22.22 |
| Level 5 | 58.62 | 61.49 | 62.56 | 58.90 | 62.39 |

As further illustrated by TABLE 3, on average the quantitation decay between Calibrator Levels 2 through 5, as measured from Day 0, were as follows:

TABLE 3

TSH Assay Stability Decay for Calibrator
Levels 2-5 In Absence of Scavenger

| Calibrator | Day 7 | Day 14 | Day 21 | Day 35 |
|---|---|---|---|---|
| Level 2 | .920 | .816 | .793 | .747 |
| Level 3 | .912 | .832 | .791 | .737 |
| Level 4 | .929 | .868 | .790 | .749 |
| Level 5 | .915 | .860 | .815 | .681 |
| Average | .919 | .844 | .797 | .729 |

In contrast the levels of decay in the presence of a scavenger remained at a constant near zero, as illustrated by TABLE 4.

TABLE 4

TSH Assay Stability Decay for Calibrator Levels
2-5 In Presence of porous Scavenger

| Calibrator | Day 7 | Day 14 | Day 21 | Day 35 |
|---|---|---|---|---|
| Level 2 | 1.010 | 1.000 | 1.010 | 1.031 |
| Level 3 | 1.039 | 1.044 | 1.014 | 1.065 |
| Level 4 | 1.065 | 1.063 | 1.041 | 1.070 |
| Level 5 | 1.049 | 1.067 | 1.005 | 1.064 |
| Average | 1.041 | 1.044 | 1.018 | 1.058 |

TABLE 5 and TABLE 6 illustrate the effects of elimination of free species in addition to the creation of signal generating networks. As previously discussed the data show a substantial increase in the immunoassay response signal with a stabilized background noise in the presence of biotin-modified sensitizer beads

TABLE 5

LOCI TSH Immunoassay Calibration Curve
SAV Sensitizer bead suspension at 1400 μg/mL
with or without biotin-modified sensitizer

| | Additive | | |
|---|---|---|---|
| | 0% | 1% | 5% |
| Calibrator | Immunoassay signal response in photon counts | | |
| Level 1 | 3534 | 3658 | 3433 |
| Level 2 | 50252 | 83150 | 93790 |
| Level 3 | 208500 | 338382 | 376341 |
| Level 4 | 996960 | 1554725 | 1738055 |
| Level 5 | 2556284 | 3818949 | 4082537 |

TABLE 6

LOCI FT3 Immunoassay Calibration Curve
SAV Sensitizer bead suspension at 400 μg/mL
with or without biotin-modified sensitizer

| Calibrator | Additive | | |
|---|---|---|---|
| | 0% | 1% | 5% |
| | Immunoassay signal response in photon counts | | |
| Level 1 | 1772532 | 2157288 | 2405371 |
| Level 2 | 1062516 | 1289000 | 1457286 |
| Level 3 | 615536 | 761405 | 874360 |
| Level 4 | 196229 | 245013 | 274417 |
| Level 5 | 8520 | 10008 | 10852 |

Based on these results, it is clear that the use of a second substrate as described greatly enhances the stability of assays over an extended period and enhances signal strength. The present invention, thereby allows for the accurate testing for analytes of interest even if the assay utilized contains a solid-phase substrate, which leaches a free species during normal storage or when exposed to unusual temperatures or motions.

Although the present invention has been described in detail with particular reference to preferred embodiments thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure, description, and tables are for illustrative purposes only, and do not in any way limit the invention, which is defined only by the claims.

We claim:

1. A method of reducing signal to noise ratio and of amplifying a signal in an assay, the method comprising:
   providing a fluid medium containing a first solid phase having at least one first binding species attached thereto; and
   providing in said fluid medium a second solid phase (i) having regions characterized by their ability to bind said first binding species if dissociated from said first substrate to scavenge said dissociated first binding species and (ii) having a binding site to bind said first binding species attached to said first solid phase to aggregate said first solid phase to produce a signal-generating network, wherein said regions characterized by their ability to bind said first binding species if dissociated from said first solid phase to scavenge said dissociated first binding species comprise pores having a size that permits access of said dissociated first binding species but excludes said first solid phase.

2. The method of claim 1, wherein said first solid phase comprises a plurality of particles.

3. A method of reducing signal to noise ratio and of amplifying a signal in an assay, the method comprising:
   providing a fluid medium containing a first solid phase having at least one first binding species attached thereto; and
   providing in said fluid medium a second solid phase (i) having regions characterized by their ability to bind said first binding species if dissociated from said first substrate to scavenge said dissociated first binding species and (ii) having a binding site to bind said first binding species attached to said first solid phase to aggregate said first solid phase to produce a signal-generating network, wherein said regions characterized by their ability to bind said first binding species if dissociated from said first solid phase to scavenge said dissociated first binding species comprise a surface modified to permit access of said dissociated first binding species but to exclude said first solid phase.

4. The method of claim 3, wherein said modified surface comprises indentations or brush-like appendages.

5. The method of claim 3, wherein said first solid phase comprises a plurality of particles.

6. A method of reducing signal to noise ratio and of amplifying a signal in an assay, the method comprising:
   providing a fluid medium containing a labeled first particle having streptavidin attached thereto; and
   providing in said fluid medium a second particle having biotin bound thereto wherein said particle has pores having a size that permits access of streptavidin if dissociated from said first particle but excludes said first particle.

* * * * *